US009606031B2

(12) United States Patent
Laugharn, Jr. et al.

(10) Patent No.: US 9,606,031 B2
(45) Date of Patent: Mar. 28, 2017

(54) SYSTEMS AND METHODS FOR TRANSFER AND PROCESSING OF BIOLOGICAL SAMPLES

(71) Applicant: Covaris, Inc., Woburn, MA (US)

(72) Inventors: James A. Laugharn, Jr., Winchester, MA (US); Guillaume Durin, Lyons (FR); Jonathan Sampson, Lynn, MA (US); Austin Purdy, Boston, MA (US)

(73) Assignee: Covaris, Inc., Woburn, MA (US)

( * ) Notice: Subject to any disclaimer, the term of this patent is extended or adjusted under 35 U.S.C. 154(b) by 251 days.

(21) Appl. No.: 14/338,976

(22) Filed: Jul. 23, 2014

(65) Prior Publication Data

US 2016/0025604 A1   Jan. 28, 2016

(51) Int. Cl.
A61B 10/00 (2006.01)
G01N 1/30 (2006.01)
G01N 1/02 (2006.01)
G01N 1/31 (2006.01)
G01N 1/40 (2006.01)

(52) U.S. Cl.
CPC ................. *G01N 1/30* (2013.01); *G01N 1/02* (2013.01); *G01N 1/31* (2013.01); *G01N 2001/028* (2013.01); *G01N 2001/4094* (2013.01)

(58) Field of Classification Search
CPC ....................................................... C12M 13/00
See application file for complete search history.

(56) References Cited

U.S. PATENT DOCUMENTS

| | | |
|---|---|---|
| 6,719,449 B1 | 4/2004 | Laugharn, Jr. et al. |
| 6,948,843 B2 | 9/2005 | Laugharn, Jr. et al. |
| 9,080,167 B2 | 7/2015 | Laugharn, Jr. et al. |
| 2008/0193926 A1 | 8/2008 | Abraham-Fuchs et al. |
| 2011/0239793 A1 | 10/2011 | Ohtsuka et al. |
| 2011/0296639 A1 | 12/2011 | Strauss |
| 2012/0015419 A1 | 1/2012 | Laugharn, Jr. et al. |
| 2013/0213154 A1 | 8/2013 | Crowder et al. |
| 2013/0295573 A1 | 11/2013 | Carrera Fabra et al. |
| 2014/0141413 A1 | 5/2014 | Laugharn, Jr. et al. |

OTHER PUBLICATIONS

Invitation to Pay Additional Fees dated Sep. 25, 2015 from corresponding International Application No. PCT/US2015/041077.

*Primary Examiner* — Jyoti Nagpaul
(74) *Attorney, Agent, or Firm* — Wolf, Greenfield & Sacks, P.C.

(57) ABSTRACT

Systems and methods are described for transfer of tissue samples from a substrate to a vessel, for subsequent processing (e.g., focused acoustic treatment) within the vessel. A transfer apparatus, having a transfer end and a handle end, may be used to collect a sample material from the substrate. When the sample material is collected from the substrate, the transfer end may be placed within a vessel for treatment of the sample material while the transfer end is also located within the vessel. In some embodiments, the transfer end may be decoupled or otherwise separated from the handle end so that only the transfer end portion of the transfer apparatus is located within the vessel during treatment.

21 Claims, 11 Drawing Sheets

SYSTEMS AND METHODS FOR TRANSFER AND PROCESSING OF BIOLOGICAL SAMPLES

BACKGROUND

1. Field

Systems and methods relating to the transfer and processing of biological samples are generally disclosed.

2. Related Art

Tissue samples, such as those taken by biopsy or other technique, are commonly formalin-fixed and paraffin embedded (FFPE) to allow for extended storage of the samples and the structure of the cell and sub-cellular components to be maintained, with relatively little degradation of DNA, RNA, proteins or other materials in the sample. In such FFPE processing, the samples are typically fixed in a formalin solution (e.g., a 10% formalin solution may contain 3.7% formaldehyde and 1.0 to 1.5% methanol), which creates crosslinks between nucleic acids, between proteins and/or between nucleic acids and proteins. Afterward, the sample is dehydrated, e.g., by placing the sample in an alcohol, and then "cleared" of the alcohol by exposing the sample to a solvent such as xylene. The sample is then embedded in paraffin, where the sample is surrounded by paraffin which replaces the xylene in the sample. The paraffin embedded sample can then be stored for extended periods of days, months, years. At a desired time, the samples may then be transferred to a vessel or other system for further processing.

Focused acoustic energy-based sample processing devices, such as Adaptive Focused Acoustic apparatuses made by Covaris of Woburn, Mass., are effective for homogenization, lysing, disruption or other processing of biological tissues, cells and other sample material. The devices are also beneficial for chemical applications, such as compound dissolution, formulation, micronization, emulsification (e.g., paraffin embedding FFPE tissues) and other processes. FFPE samples, or other biological samples, may be processed using focused acoustics.

SUMMARY

The inventors have recognized and appreciated that it would be advantageous to transfer small portions of a biological sample (e.g., tissue, cells, etc.) from a substrate, on which the sample initially resides, to a vessel, in a manner that is efficient, while reducing the likelihood of sample contamination. Upon suitable transfer from the substrate to the vessel, the sample may be processed (e.g., using focused acoustic treatment) accordingly.

In certain embodiments, the device or instrument that is used to collect the sample is placed along with the sample in the vessel and processed together with the sample. Accordingly, the sample need not be removed or transferred yet another time, from the initial device that collects the sample from the substrate. The ability for the sample to be transferred only once may provide for increased sample recovery. Other advantages may also be apparent. For instance, the part of the device that is placed within the vessel may be structured or otherwise formed in a way that enhances sample processing. For example, in the case of focused acoustic treatment, the device may include nucleation features that serve to concentrate focused acoustic energy at particular location(s) within the vessel.

In various embodiments, a transfer apparatus may be used to collect a sample material from a substrate. The transfer apparatus may include a transfer end that may be placed in contact with the sample material, for transfer of a portion of the sample material thereto. The transfer apparatus may also include a handle end for suitable positioning or other manipulation of the transfer apparatus.

In some embodiments, the transfer apparatus may include an actuator coupled to the transfer end. The actuator may be configured to manipulate the transfer end to move between a retracted position and an extended position. When the transfer end is in a suitably extended position or otherwise sufficiently exposed for collection of a sample material, the handle end may be grasped (e.g., by hand, machine, or other suitable grip) so as to position the transfer end in contact with the sample material, for transfer of at least a portion of the sample material thereto.

Upon suitable collection of the sample material, the transfer end may be positioned within an internal volume defined by a vessel, for subsequent treatment of the sample material within the vessel, while the transfer end of the transfer apparatus is also located within the vessel.

In some embodiments, the transfer apparatus may include a first coupling portion connected to the transfer end and a second coupling portion connected to the handle end. The first and second coupling portions may be complementary to each other, permitting coupling and decoupling of one another. Upon collection of a desired amount of sample material on the transfer end, the transfer end may be decoupled from the handle end and placed within a vessel. Accordingly, the sample material and transfer end of the transfer apparatus may remain within the internal volume of the vessel for suitable treatment thereof, separate from the handle end.

When the sample material and transfer end are suitably located within the internal volume of the vessel, the contents of the vessel may be processed according to any suitable method. In some embodiments, the contents of the vessel are subject to focused acoustic energy. For example, an acoustic energy source may be configured to generate focused acoustic energy having a frequency of about 100 kHz to 100 MHz through a wall of the vessel to expose the sample material to a focal zone of acoustic energy located within the internal volume of the vessel, while both the transfer end of the transfer apparatus and sample material are both located therein.

In an illustrative embodiment, a method of processing a sample is provided. The method may include placing a transfer end of a transfer apparatus in contact with a sample material supported by a substrate. The method may further include transferring at least a portion of the sample material from the substrate to the transfer end of the transfer apparatus, and positioning the transfer end of the transfer apparatus within an internal volume of a vessel. The method may also include transmitting focused acoustic energy having a frequency of about 100 kHz to 100 MHz from an acoustic energy source through a wall of the vessel to expose the portion of the sample material to a focal zone of acoustic energy while the transfer end of the transfer apparatus and the portion of the sample material are located within the internal volume of the vessel.

In another illustrative embodiment, an acoustic treatment system is provided. The system includes a transfer apparatus. The transfer apparatus may include a transfer end constructed and arranged to be placed in contact with a sample material supported by a substrate, for transfer of at least a portion of the sample material from the substrate to the transfer end. The transfer apparatus may further include a handle end located opposite the transfer end. The handle end may be arranged to be manipulated by hand. A first coupling portion may be connected to the transfer end, and a second coupling portion may be connected to the handle end and may be complementary to the first coupling portion. The first and second coupling portions may be constructed and arranged to be coupled to and decoupled from each other. The system may further include a vessel defining an internal volume for holding the transfer end of the transfer apparatus, and an acoustic energy source configured to generate focused acoustic energy having a frequency of about 100 kHz to 100 MHz through a wall of the vessel to expose the portion of the sample material to a focal zone of acoustic energy while the transfer end of the transfer apparatus and the portion of the sample material are located within the internal volume of the vessel.

In another illustrative embodiment, a transfer apparatus is provided. The transfer apparatus may include a transfer end constructed and arranged to be placed in contact with a sample material supported by a substrate, for transfer of at least a portion of the sample material from the substrate to the transfer end. The transfer apparatus may further include a handle end located opposite the transfer end, the handle end arranged to be manipulated by hand. The transfer apparatus may include a first coupling portion connected to the transfer end, and a second coupling portion connected to the handle end and complementary to the first coupling portion. The first and second coupling portions may be constructed and arranged to be coupled to and decoupled from each other. The transfer apparatus may further include an actuator coupled to the transfer end. The actuator may be configured to manipulate a position of the transfer end between a retracted position and an extended position.

Other advantages and novel features of the present disclosure will become apparent from the following detailed description of various non-limiting embodiments when considered in conjunction with the accompanying figures and claims.

BRIEF DESCRIPTION OF THE DRAWINGS

Aspects of the present disclosure are described with reference to the following drawings in which numerals reference like elements, and wherein.

DETAILED DESCRIPTION

Figure 1:
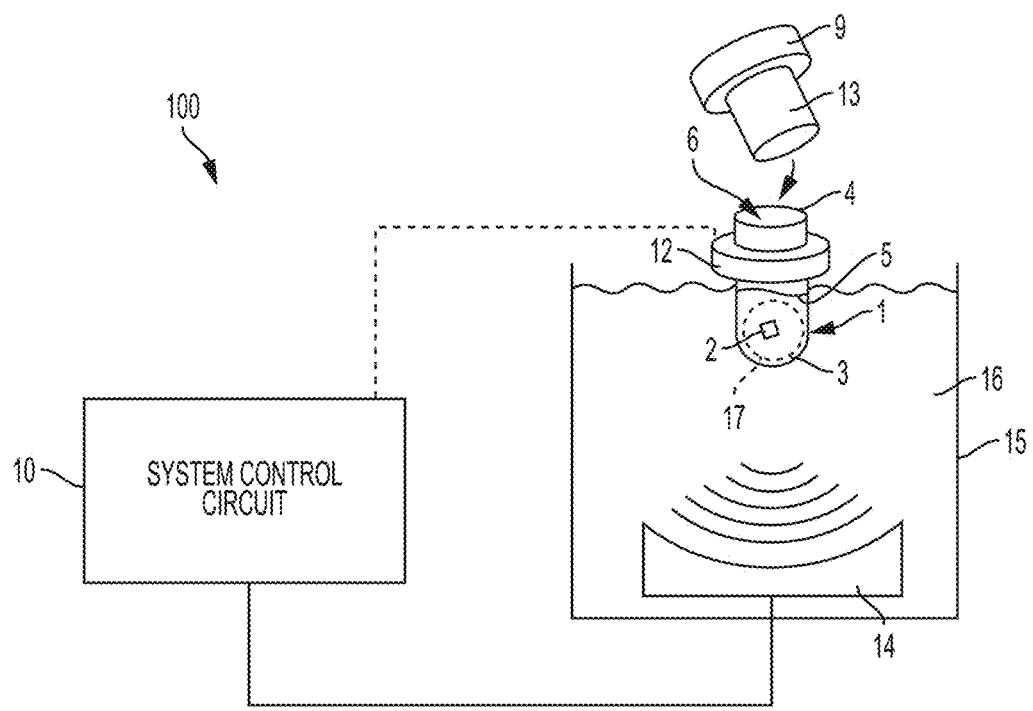
FIG. 1 shows a schematic block diagram of an acoustic treatment apparatus.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, aspects of the present disclosure may be used alone or in any suitable combination with each other. Thus, the phraseology and terminology used herein is for the purpose of description and should not be regarded as limiting.

The present disclosure relates to the transfer of a biological sample from a substrate (e.g., slide, glass surface, plate, container, etc.) to a transfer apparatus, and then placement of the biological sample, together with a transfer end of the apparatus, within a vessel for subsequent processing (e.g., focused acoustic processing). Various embodiments of the transfer apparatus provide for sterile transfer of the biological sample from the substrate to a treatment vessel, with high recovery (e.g., 90-100% recovery), and without contamination or electrostatic charge build up on the sample. Embodiments of the present disclosure may provide other advantages as well.

This is in contrast with conventional methods of sample transfer, which typically involve direct physical transfer via an adhesive composition (e.g., glue, adhesive tape, solvent-based adhesives, etc.) or a metal surface (e.g., tweezers, scalpel, razor blade, etc.). Such traditional methods of sample transfer are associated with a number of problems. The use of an adhesive composition and/or metal surface may increase the likelihood that the sample material becomes contaminated and/or physically altered in an undesirable manner.

For instance, an adhesive composition may invite the adhesion of foreign materials thereon or, by adhering to the biological sample, the adhesive composition may physically alter the sample surface and/or conformation of the sample itself (e.g., the sample may become deformed). The use of a metal surface to collect the sample material may give rise to electrostatic discharge on the surface of the sample, which may also lead to attraction of foreign materials and/or undesirable modification of the sample material. Further, once the sample material is collected on to such surfaces, it may be challenging for the sample material to be removed therefrom, for suitable transfer to a vessel for additional processing.

In accordance with aspects of the present disclosure, a transfer apparatus may be used to collect a sample material from a substrate, and deposit the sample material into a vessel, for further sample treatment. The transfer apparatus may include a transfer end that may be placed in contact with the sample material so that a portion of the sample material may be collected on to the transfer end. The transfer apparatus may also include a handle end that enables a user or other apparatus (e.g., robotic system/handler) to grasp the transfer apparatus and position it as suitably desired.

In some embodiments, the transfer apparatus may include an actuator coupled to the transfer end, for manipulating the transfer end between a retracted position and an extended position. When in the extended position, the transfer end may protrude outward a sufficient amount (e.g., from a housing) so as to facilitate collection of sample material on to the transfer end. While, in some cases, the transfer end may still be able to collect sample material in the retracted position, the ease of collection when the transfer end is in the extended position can be significantly greater.

When a desired amount of sample material is collected on to the transfer end of the transfer apparatus, the transfer end, along with the portion of sample material collected thereon, may be placed within an internal volume of a treatment vessel. In some embodiments, the transfer end and the handle end of the apparatus may be separated from one another, for example, when the transfer end and sample material are placed within the treatment vessel for further processing.

For instance, the transfer end carrying the sample material may be cut from the handle end, and dropped into the vessel. Or, complementary coupling portions (e.g., threaded regions, slotted arrangements, interference/friction fittings, etc.) respectively connected to each of the transfer end and the handle end may be decoupled from one another, separating the handle end from the transfer end. For example, the handle end may be reused with optionally disposable transfer ends. In some cases, the transfer end of the apparatus is pushed through a septum or other sealing member of the vessel and, when appropriately situated within the internal volume of the vessel, the handle end may be withdrawn therefrom, leaving only the transfer end carrying the sample material in the vessel.

Then, while the transfer end of the transfer apparatus and the sample material are both located within the vessel, the contents of the vessel may be subject to any suitable treatment or processing. The sample material may be subject to any of a number of suitable treatment steps, for example, focused acoustic treatment, radiation treatment (e.g., ultraviolet, infrared, visible light, etc.), mechanical treatment (e.g., centrifugation, vibration, applied compressive or vacuum pressure, etc.), spectroscopic analysis, or any other appropriate sample treatment.

Aspects of the present disclosure may be applicable to any suitable sample material, which may be prepared by any appropriate manner. For example, the sample material may include soft tissue, hard tissue, cells, other biological material, or certain non-biological materials. In some cases, before mounting on to a substrate, the sample material may be subject to any suitable treatment, for example, freezing, filtration, staining, fixing, embedding, purification, etc. Any suitable substrate may be used, for example, a glass slide with or without a biological and/or polymeric coating (e.g., silane, poly-L-lysine coating), or another appropriate substrate.

For instance, as discussed above, a tissue sample may be fixed or otherwise stabilized (e.g., with formalin and/or paraffin embedding, FFPE) so as to prevent decay or degradation, allowing for preservation/stabilization of the tissue for subsequent analysis/examination, with relatively little degradation of DNA, RNA, proteins or other materials in the sample. A fixation agent may be used to protect the tissue sample from damage, for example, by disabling intrinsic biomolecules, such as proteolytic enzymes which may otherwise lead to digestion or degradation of the sample. Such stabilization may also make the tissue permeable to staining reagents and amenable to cross-linking so that various macromolecules within the tissue become more stabilized. Fixation agents other than formalin may be used, such as glutaraldehyde or a freezing agent (e.g., liquid nitrogen).

When used properly, fixatives may reduce the probability of colonization of the tissue by commonly occurring microorganisms (e.g., bacteria) that may be present in or around the tissue. In some cases, a fixation agent increases the mechanical strength or stability of the tissue, which may help to preserve the overall shape and structure of the sample as it is processed.

The tissue sample may be stored for a suitable period of time. For example, if formalin fixed and paraffin embedded, the sample may be stored for relatively long periods of time (e.g., weeks, months, years) without suffering degradation or damage. The ability to retain histological quality of the transferred portion of the sample (e.g., immunohistochemically stained) may allow for various types of analyses and diagnoses to be performed. For instance, a sample may be analyzed so as to obtain a diagnosis as to whether the tissue is normal or malignant. Alternatively, or in addition, the tissue sample may be subject to any suitable molecular analyses (e.g., sequencing, biomarkers, etc.).

When the sample is embedded in paraffin, the overall temperature of the sample during processing may remain below a melting temperature of the paraffin. As a result, in some embodiments, paraffin may be disassociated from tissue sample material without causing bulk melting of the paraffin. Also, if the paraffin embedded sample is surrounded by an aqueous solution (non-solvent liquid), the sample may be rehydrated during paraffin disassociation. For example, exposing the sample to focused acoustic energy during a paraffin disassociation process may result in an opalescent-appearing liquid as the paraffin is emulsified or otherwise separated from tissue portions of the sample.

Accordingly, portions of frozen, fixed and/or (paraffin) embedded archival tissue may be transferred from a substrate to a treatment vessel, without appreciable damage or alteration. Examples of paraffin embedded tissue samples and acoustic processing thereof are described in U.S. application Ser. No. 13/678,755, entitled "System and Method for Processing Paraffin Embedded Samples," assigned to Covaris of Woburn, Mass., and may be incorporated in systems described herein.

Also, systems of the present disclosure may be used for other additional types of focused acoustic processing of a sample, such as for mixing or DNA/RNA shearing, for example, to reduce the base pair length of DNA fragments from 1,000 s or 10,000 s of base pairs to lengths of 3 k base pairs or smaller, in a reproducible and high-yield manner, and/or to extract biological molecules from the sample. Examples of such acoustic treatment systems and control arrangements are described in U.S. Pat. Nos. 6,948,843 and 6,719,449, assigned to Covaris of Woburn, Mass., and may be incorporated in systems described herein.

FIG. 1 shows a schematic block diagram of an acoustic treatment system 100 that incorporates various features that may be used with one or more aspects of the present disclosure. Various details of the acoustic treatment system 100, schematically depicted in FIG. 1, are provided further below. It should be understood that although embodiments described herein may include some or all aspects of the present disclosure, aspects of the present disclosure may be used alone or in any suitable combination with other aspects of the present disclosure.

Figure 2:
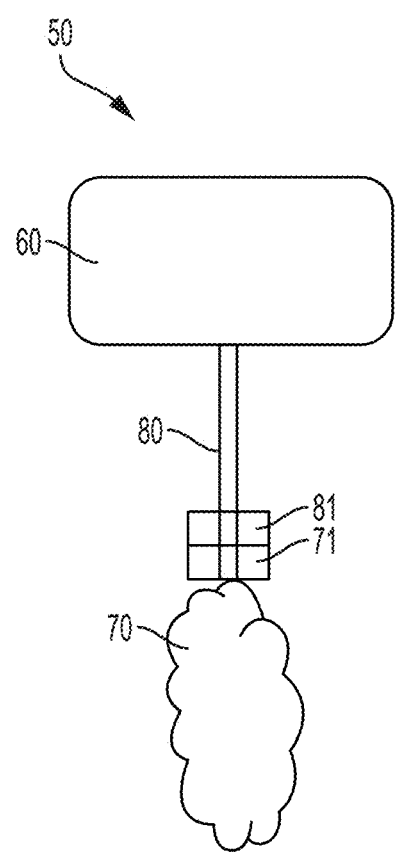
FIG. 2 illustrates a transfer apparatus in accordance with an embodiment.

FIG. 2 shows a transfer apparatus 50 having a handle end 60 and a transfer end 70, with a shaft 80 connecting the two ends. In some embodiments, as discussed further below, portions of the shaft 80 may be detached or otherwise decoupled in a suitable manner so as to separate the transfer end 70 from the handle end 60. For example, in this embodiment, a first coupling portion 71 connected to the transfer end 70 may be coupled to a second coupling portion 81 connected to the handle end 60. The first and second coupling portions 71, 81 may be decoupled to separate the transfer end 70 from the handle end 60.

In certain embodiments, the handle end 60 may include a bar, cap, gripping surface, knob-like or other suitable handle structure that is suitable for grasping and manipulating of the transfer apparatus, by a user or machine. For example, as shown in FIG. 2, the handle end 60 may include a cap or other structural feature having a surface that extends perpendicular to the longitudinal direction along which the shaft 80 extends, allowing for the handle end 60 to be easily grasped.

The transfer end 70 includes a collecting portion/material that is appropriately structured to facilitate transfer of a sample material from a substrate thereto. As illustratively provided in FIG. 2, the transfer end 70 may include a fibrous surface or other suitable material on which the sample material may adhere or otherwise be collected. In some embodiments, the transfer end 70 includes a microfiber composition suitable for collecting a portion of sample material from a supporting substrate, when placed in appropriate contact. For example, the transfer end 70 may include a soft, non-abrasive aggregate of microfibers (e.g., similar to a cotton swab) suitable for sample collection.

Figure 8A:
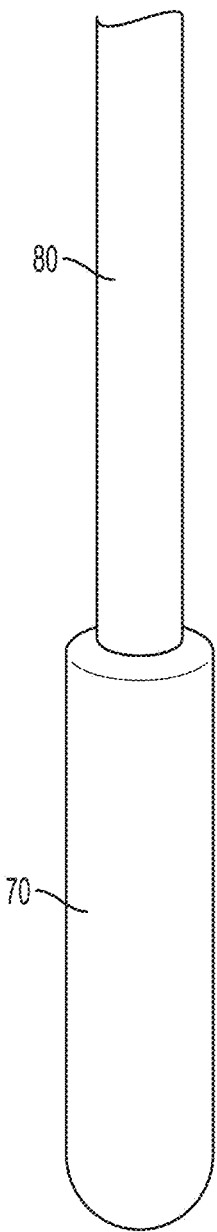
FIG. 8A illustrates a portion of another transfer apparatus in accordance with an embodiment.

The transfer end 70 may include any suitable material. In some embodiments, the transfer end may include a polymeric material, such as polyester, polyethylene, ultra high molecular weight polyethylene, polypropylene, polytetrafluoroethylene, nylon, or any other appropriate composition. In some embodiments, the transfer end 70 may include a suitably rigid surface that provides an appropriate amount of mechanical support, for dislodging the sample material from the substrate, as well as holding the sample material in place when collected. Yet, the transfer end 70 may also include a material that is soft and absorbent enough for sample collection thereon. For example, as shown further below in FIG. 8A, the transfer end 70 may include an appropriately stiff shaft 80 that is covered with a microfibrous web.

As discussed herein, both the length and width (e.g., diameter) of the transfer end may be sized to fit and move freely within the treatment vessel during processing (e.g., focused acoustic treatment). In general, the length and width of the transfer end may be large enough to facilitate easy and effective collection of sample material from the substrate, yet small enough so as not to interfere with processing of the sample within the vessel. Further, to facilitate removal of sample material from a substrate, the core of the transfer end may be relatively dense and rigid. Though, the exterior of the transfer end may include a microfibrous web, allowing for sample cohesion thereto.

Figure 8B:
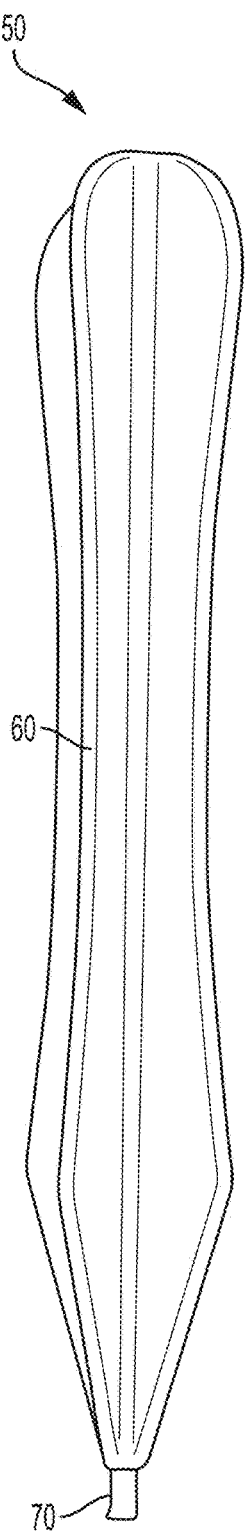
FIG. 8B depicts another transfer apparatus in accordance with an embodiment.

FIG. 8B shows another example of a transfer apparatus 50 where the transfer end 70 includes a cylindrical rod approximately 5.0 mm in length and approximately 1.37 mm in diameter. In this example, 2.0 mm of the rod is exposed, for collection of sample material, while the remainder of the rod is firmly secured by one or more holding components (not expressly shown in the figures) of the transfer apparatus. As further shown, the handle end 60 of the transfer apparatus is shaped for suitable grasping and manipulation thereof by an operator.

As the transfer end 70 and the sample material are both located within the vessel during subsequent treatment, it can be appreciated that the transfer end 70 may incorporate a suitable material/structure that is compatible with or, in some cases, enhances the particular type of treatment. For example, in some embodiments, the transfer end 70 may include a non-woven, hydrophobic material which may, in some cases, provide nucleation sites for the formation of bubbles or cavitation when subject to focused acoustic treatment. Or, in other embodiments, the transfer end 70 may be suitably transparent or translucent, so as not to interfere with radiative treatment(s) and/or spectroscopic analyses.

As noted above, a number of problems may be associated with conventional methods of collecting and transferring sample material. For instance, using an adhesive peel and/or metal surface, such as a razor blade, to remove sample material from a substrate may lead to contamination of the sample as well as difficulty in transferring the sample to an appropriate vessel for further processing. As noted above, the use of metal or conductive surfaces to remove the sample material may also lead to electrostatic build up on the sample material which, in some cases, may attract surrounding particulate debris, resulting in sample contamination.

Embodiments of the present disclosure may alleviate such problems. Using suitable transfer apparatuses and methods described herein, a sample material may be kept sterile when transferred from a substrate to the transfer end, and also when deposited, with the transfer end, into a vessel for additional processing. For instance, upon collection of the sample material from the substrate to the transfer end, the sample material may be kept free from substantial electrostatic build up, limiting the possibility of attraction of surrounding contaminants.

FIGS. 3-6 depict illustrative embodiments of a transfer apparatus 50 in use, where a sample material 2 is transferred from the surface of a substrate 20 to the transfer end 70 and the transfer end, together with the sample material, is deposited into the vessel for ensuing focused acoustic processing.

Figure 3:
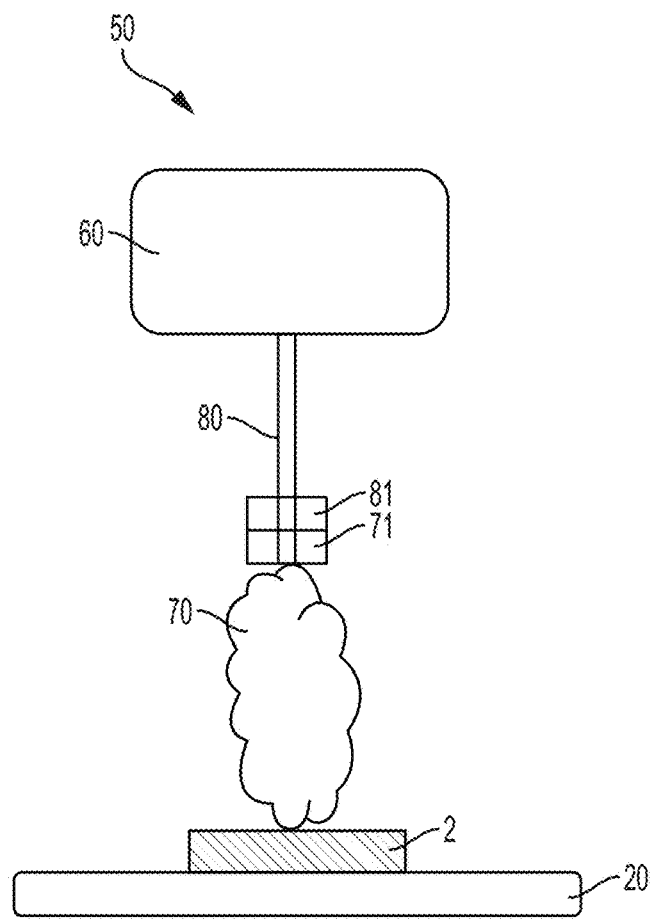
FIG. 3 depicts use of the transfer apparatus of FIG. 2 with a sample on a substrate in accordance with an embodiment.

As shown in FIG. 3, the transfer apparatus 50 is positioned such that the transfer end 70 is placed in contact with the sample material 2, for collection of a portion thereof. In some embodiments, prior to collection of the sample material 2 on to the transfer end 70, the sample material 2 and/or the transfer end 70 may treated with an appropriate transfer agent for (re)hydrating, softening and loosening of the sample from the substrate 20.

Such an agent may include a solution, solvent, buffer, any other suitable composition, or combination thereof, that facilitates transfer of sample material from the substrate to the transfer apparatus. For example, the transfer agent may include a solution that at least partially soaks into the sample material and then evaporates, resulting in loosening of the sample material from the substrate, while leaving little to no residue. Similarly, when the agent is applied to the transfer end of the transfer apparatus, upon contact of the transfer end with the sample material, the loosening effect of the agent may assist removal of the sample material from the substrate.

As an example, CitriSolv™ is a clearing solvent, containing limonene, that is biodegradable and may be used in histology, cytology, hematology and microbiology applications, for dissolving paraffin wax and/or adhesives, without leaving residue. Such a composition may be suitable for use as a transfer agent to aid in transfer of the sample material. Alternatively, or in addition, a suitable buffer (e.g., 0.1-1.0% sodium dodecyl sulfate buffer) may be used as a transfer agent for removal of the sample material from the substrate. Other transfer agents may include, for example, limonene, solutions/solvents containing citric acid, surfactants, aqueous buffers, or other compositions. It can be appreciated that any other suitable composition for facilitating transfer of the sample material may be employed. In various embodiments, it may be preferable to use transfer agents that do not interfere with downstream processes, such as purification, nucleic acid extraction, focused acoustic treatment and/or other procedures.

In some embodiments, the amount of transfer agent used may be just enough to soak the fibrous web of the transfer end. For example, in the example shown in FIG. 8B, approximately 3 microliters of transfer agent may be used to saturate a microfibrous transfer end where approximately 1.37 mm in length is exposed for sample collection. Though, it can be appreciated that the amount or concentration of transfer agent used may depend on the type of sample material being processed and the nature of the transfer end used to collect the sample. In some cases, a transfer agent is not necessary.

As noted above, for some embodiments, the transfer agent(s) may be applied to the transfer end of the transfer apparatus and/or the sample material. For example, CitriSolv™ (e.g., 50%, 100% CitriSolv™ in aqueous solution), buffer (e.g., sodium dodecyl sulfate), or other suitable composition, may be applied to the transfer end of the transfer apparatus (e.g., via pipette, spray, syringe, pouring, dipping, etc.), to prepare the transfer end for collection of sample material from a substrate. In some cases, it may be preferable for the sample material itself to be treated with a suitable transfer agent. For instance, an appropriate amount of CitriSolv™, buffer, or other suitable composition, may be applied to the sample material (e.g., via pipette, spray, syringe, pouring, dipping, etc.).

Once the sample material and/or the transfer end of the transfer apparatus are optionally treated, as desired, the transfer end of the transfer apparatus may be moved into contact with the sample material. In some cases, the transfer end is pressed against the sample material, for collection thereon, in a non-destructive manner. For example, the transfer end may be rubbed against (e.g., whipped, rotated, swept, etc.) the sample material so that a suitable portion of the sample is dislodged from the substrate and adhered or otherwise collected on to the transfer end.

The temperature of or around the sample material and/or transfer end of the transfer apparatus may be adjusted to better accommodate collection of the sample material from the substrate to the transfer end. In some cases, the transfer agent may be more effective to enhance loosening of the sample material from the substrate at certain temperatures. In some embodiments, during transfer, the temperature of the surrounding environment, or the sample material itself, may be set to between 10° C. and 80° C., between 20° C. and 70° C., between 30° C. and 60° C., between 30° C. and 50° C., or other suitable temperature ranges. For example, CitriSolv™ may be effective to suitably cause loosening of the sample material from the substrate at approximately 40° C., for collection by a transfer end (e.g., nylon swab). The temperature may be suitably adjusted via a hot plate, temperature chamber, environmental controls, etc. Other suitable temperatures outside of the above noted ranges may be employed.

The transfer apparatus may be used to collect and transfer any suitable sample material. For example, as noted above, the sample material may be a FFPE tissue sample located on a slide, container, or other substrate. Alternatively, the sample may be tissue (e.g., buccal tissue, biological remains/tissue, etc.) collected directly from a source (e.g. inside of a mouth, surface of a crime scene), and/or from a preserved or sectioned sample (e.g., previously collected and stored). In some embodiments, the sample material may include fungal and/or bacterial cultures, for collection and transfer from an agar plate. Though, it can be appreciated that aspects of the present disclosure may be applied to any other suitable sample materials where a portion may be collected and transferred to a vessel for subsequent processing.

Figure 4:
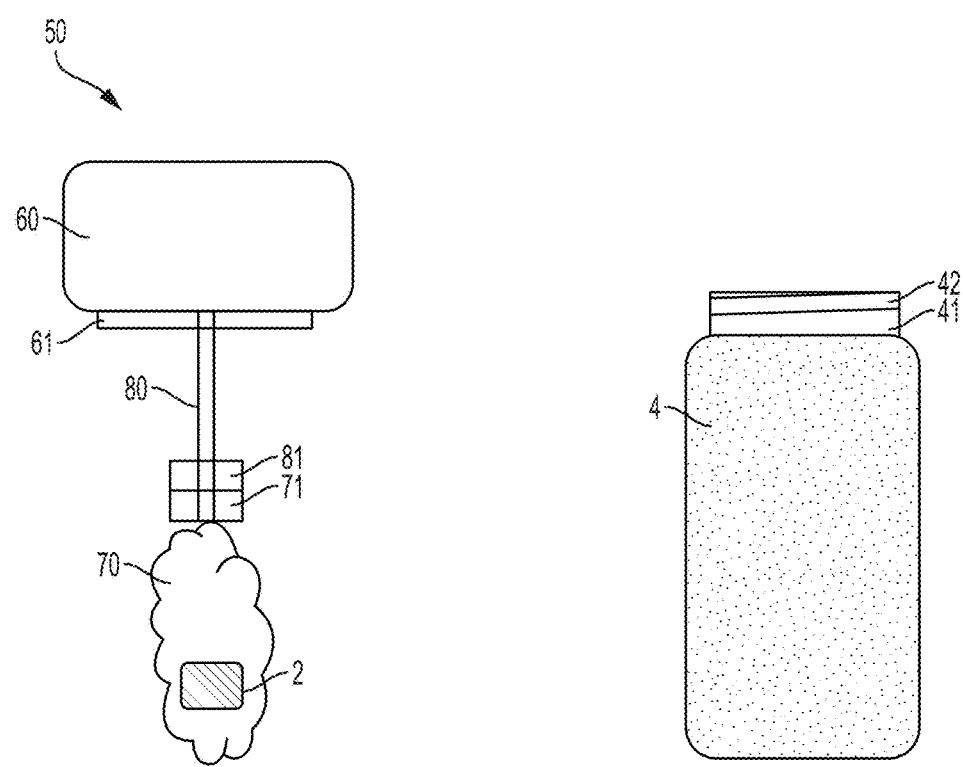
FIG. 4 shows use of the transfer apparatus of FIGS. 2-3 with a vessel in accordance with an embodiment.

FIG. 4 depicts the transfer apparatus 50 after a portion of sample material 2 has been collected on to the transfer end 70. It can be appreciated that, in some cases, the transfer apparatus 50 may be suitably structured and manipulated to collect the entire contents of the sample material from the substrate. As shown, the transfer end 70, along with the sample material 2, is ready for insertion into the vessel 4.

In some embodiments, the vessel 4 includes a buffer and/or other suitable solution/solvent for use during subsequent sample treatment. For example, in the case of focused acoustic treatment, it may be preferable for the internal volume of the vessel within which an acoustic focal zone may be formed to include an appropriate buffer solution (e.g., phosphate buffered saline, sodium dodecyl sulfate solution).

Figure 5:
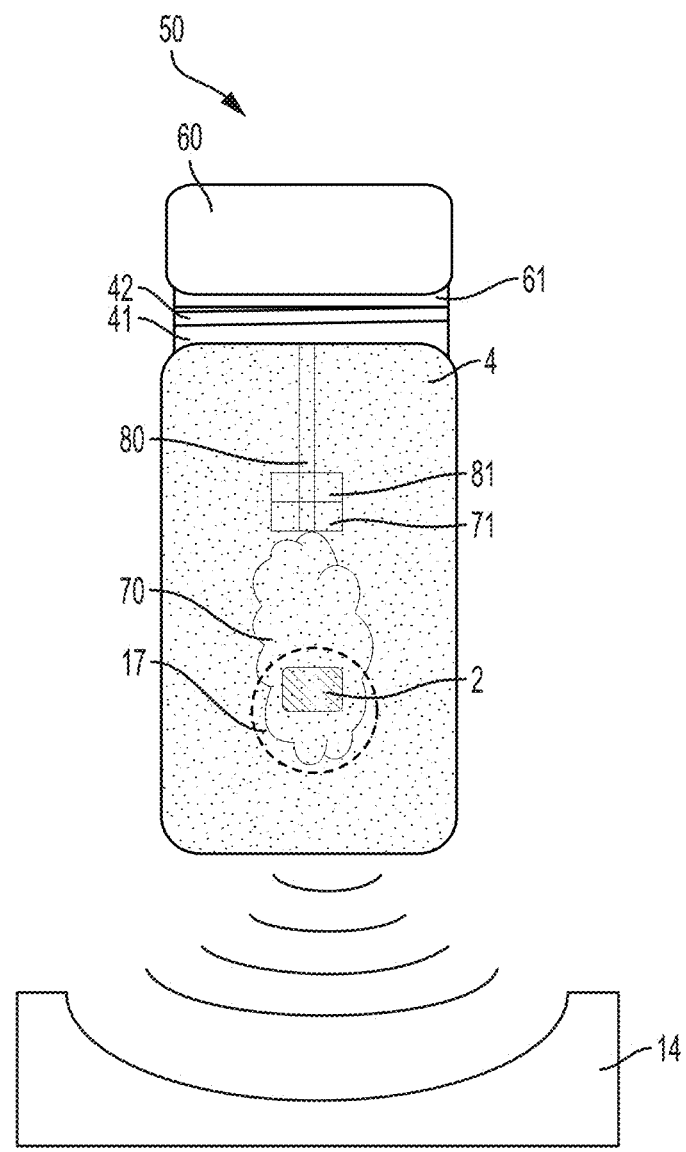
FIG. 5 shows use of the transfer apparatus and vessel of FIG. 4 with an acoustic treatment system in accordance with an embodiment.

In FIG. 5, the transfer apparatus 50 is coupled to the vessel 4 such that the transfer end 70 and the sample material 2 are located within the internal volume of the vessel 4. In this embodiment, the handle end 60 has a first fastening region 61 that is arranged to be fastened to a second fastening region 42 at an entrance portion of the vessel 4. An acoustic transducer 14, described in more detail further below, is configured and arranged to generate acoustic energy converging at a focal zone 17 that is located, at least partially, within the internal volume of the vessel 4. Thus, the sample material 2 is exposed to the acoustic focal zone 17, and processed accordingly.

Figure 6:
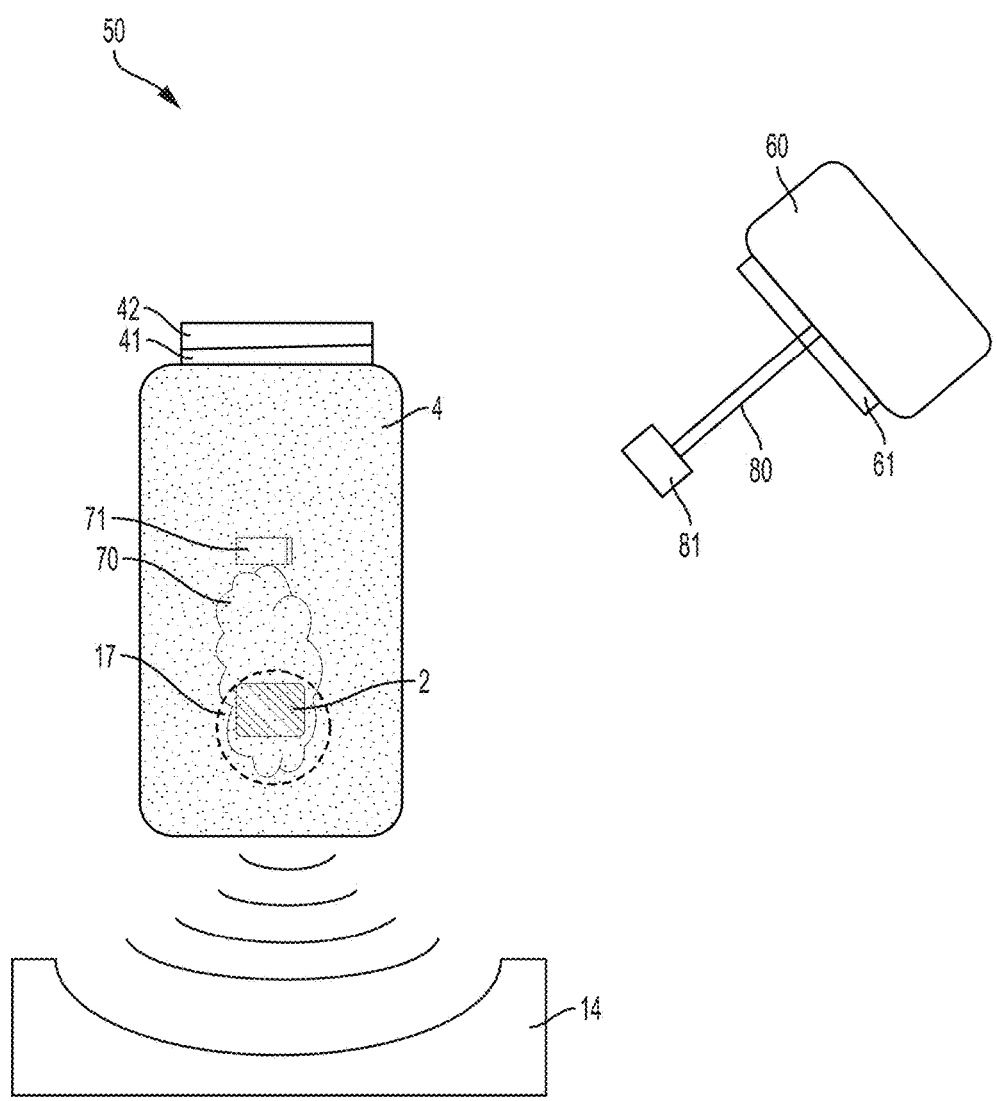
FIG. 6 shows another use of the transfer apparatus and vessel of FIG. 4 with an acoustic treatment system in accordance with an embodiment.

In some embodiments, after collection of the sample material, and either before or after placement of the transfer end 70 within the vessel, the handle end 60 and the transfer end 70 of the transfer apparatus 50 may be separated from one another. FIG. 6 shows an example of a transfer apparatus where the handle end 60 and the transfer end 70 are separated from one another.

In some embodiments, the shaft 80 connecting the handle and transfer ends is severed or cut and the transfer end, together with the sample material, are placed in the vessel. For example, once the handle end is removed, the transfer end and sample material may be dropped, pushed or otherwise left in the vessel, absent the handle end.

In some embodiments, such as that shown in FIGS. 2-6, the transfer end 70 may include or be connected to a first coupling portion 71, and the handle end 60 may include or be connected to a second coupling portion 81. The first and second coupling portions 71, 81 may be complementary to one another such that the transfer end 70 and handle end 60 may be coupled and decoupled, as desired. For example, when the transfer end 70 and handle end 60 are attached or otherwise coupled together, via respective coupling portions 71, 81, the transfer and handle ends may be rigidly connected. In some embodiments, coupling and decoupling of the transfer and handle ends is reversible.

The coupling portions may include any suitable structure that allows for assembly and disassembly of the transfer apparatus. One or more of the complementary coupling portions may include, for example, a bolt, nut, threaded region, biasing member, slot, rivet, fastener, adhesive, or any other suitable structures that allow the transfer and handle ends to be secured together. And, when desired, the transfer and handle ends may be separated from one another.

For instance, the shaft between the transfer end and handle end may include complementary threaded regions that allow the transfer and handle ends to be screwed together and unscrewed, as appropriate. Or, the coupling portion of the transfer end may form a snap fit arrangement with the coupling portion of the handle end, allowing for quick and easy attachment and detachment therebetween. In some embodiments, the handle end, or other part of the transfer apparatus, may have a button or other actuator that causes separation or release of the transfer end from the handle end. In some cases, the transfer end may be press fit with the handle end and an integrated or separate plunger mechanism may be employed to eject the transfer end from the apparatus and into the vessel. It can be appreciated that the transfer and handle ends may be mutually coupled and decoupled in any suitable manner.

In some embodiments, the handle end of the transfer apparatus is reusable. For example, a sterile, disposable transfer end may be attached or coupled to the handle end to form a suitable transfer apparatus. Once assembled, the transfer apparatus may be appropriately manipulated, with optional treatment with a transfer agent, to collect sample material from a substrate. The handle end is withdrawn from the assembly once the transfer end together with the sample material are deposited within the treatment vessel, for further processing. The handle end of the transfer apparatus may then be coupled to another sterile transfer end, for collection and transfer of another sample material.

In some embodiments, the vessel may include a sealing member 41 shown in FIG. 4, such as an elastomeric septum, o-ring or other appropriate structure, that accommodates entry of the transfer end of the transfer apparatus into the internal volume of the vessel. For instance, a rubber septum may be pierced or may have a slot through which the transfer end may penetrate into the vessel. Once the transfer end carrying the sample material has entered through the septum, or other sealing member, and is suitably located within the vessel, whether the transfer end is coupled or decoupled with respect to the handle end, the sealing member may optionally provide a seal for the internal volume of the vessel from the surrounding external environment.

In some cases, the transfer end may be separated from the handle end, and then fitted through the sealing member into the vessel. Or, prior to separation, the transfer apparatus may be manipulated, via the handle end, such that the transfer end with sample material is placed within the vessel (e.g., pushed through or past the sealing member). When the transfer end is suitably positioned, the handle end may be withdrawn from the vessel, and optional sealing member. For example, the handle end may be pulled so as to withdraw the shaft from the vessel, allowing the transfer end to slide off or otherwise decouple from the shaft and handle end, remaining therein. Or, the transfer end may be released from the handle end, so as to remain within the vessel, where separation occurs, for example, by depressing an appropriately configured button.

When the transfer end of the transfer apparatus is dropped or otherwise positioned within the internal volume of the vessel, having been separated from the handle end, in some cases, the transfer end may be pushed further down toward the bottom wall of the vessel. In some embodiments, it may be preferable for the transfer end to be suitably positioned near the bottom of the internal volume of the vessel, for subsequent processing thereof. For example, when subject to focused acoustic treatment, it may be desirable for the sample material to be positioned where the focal zone of acoustic energy is formed.

Figure 7:
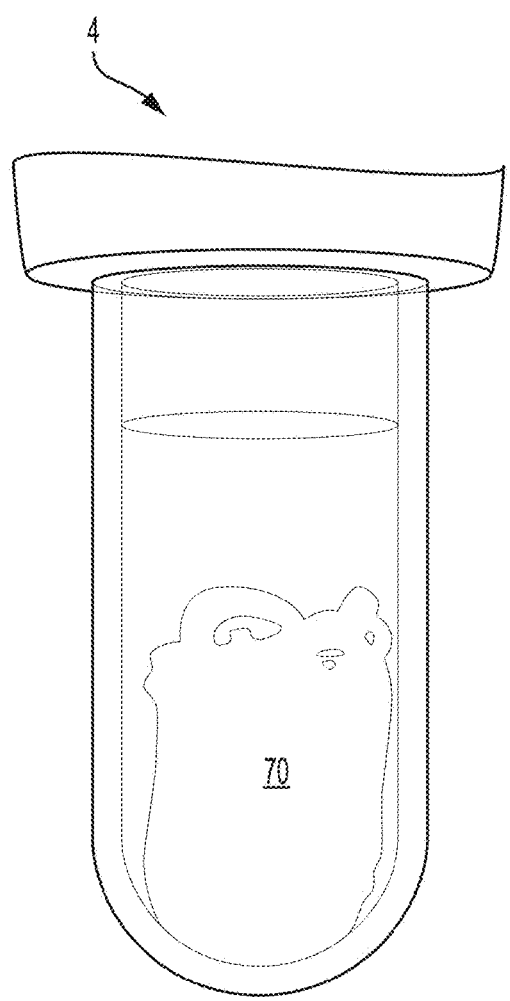
FIG. 7 shows use of another transfer apparatus in accordance with an embodiment.

Accordingly, in some cases, the transfer end may be attached or otherwise coupled to a portion of the vessel within the internal volume, to be appropriately held in place at a desirable location for sample treatment. For instance, as shown in FIG. 7, when a transfer end 70 including a fibrous swab carrying sample material is pushed against the bottom wall of the vessel, the sample material is held in place during processing (e.g., exposure to focused acoustic energy) thereof. As noted above, the structure of the transfer end 70 may be suitable to further enhance focused acoustic treatment of the sample, for example, by lowering the threshold for bubble nucleation or cavitation.

FIG. 8 illustrates an embodiment of the transfer end 70 of a transfer apparatus, provided as a padded swab. In this embodiment, the swab is slidably fit over a shaft 80, which connects the transfer end 70 to a handle end (not shown in this figure). The swab includes a microfiber aggregate that forms a web that facilitates collection of sample material from a substrate. The microfibrous web is soft enough such that the sample material remains undamaged when transferred thereto, and the underlying shaft 80 is stiff enough to provide a suitable degree of support and rigidity for the microfibrous web, for example, to dislodge the sample material from the substrate.

As noted above, in some cases, the microfibrous web may be constructed to slide off of the shaft upon application of a suitable amount of shear. For example, as also described above, the vessel may include a cap and/or septum for keeping materials suitably contained within the internal volume. When the transfer end 70 is placed within the vessel, the shaft 80 may be pulled outward such that the cap or septum of the vessel obstructs the transfer end 70 from exiting the vessel. Accordingly, as the transfer end slides off of the shaft and remains within the vessel, the shaft, handle end, and other parts of the transfer apparatus are removed therefrom.

Figure 9A:
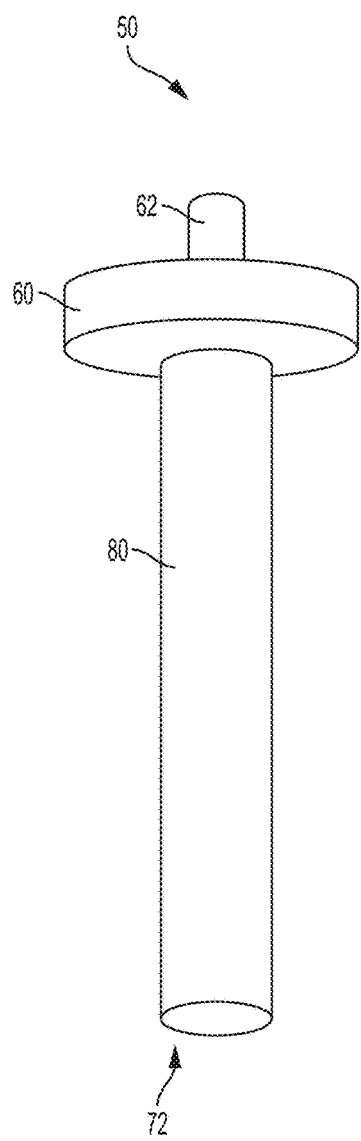
FIGS. 9A-9B depict use of yet another transfer apparatus in accordance with an embodiment.
Figure 9B:
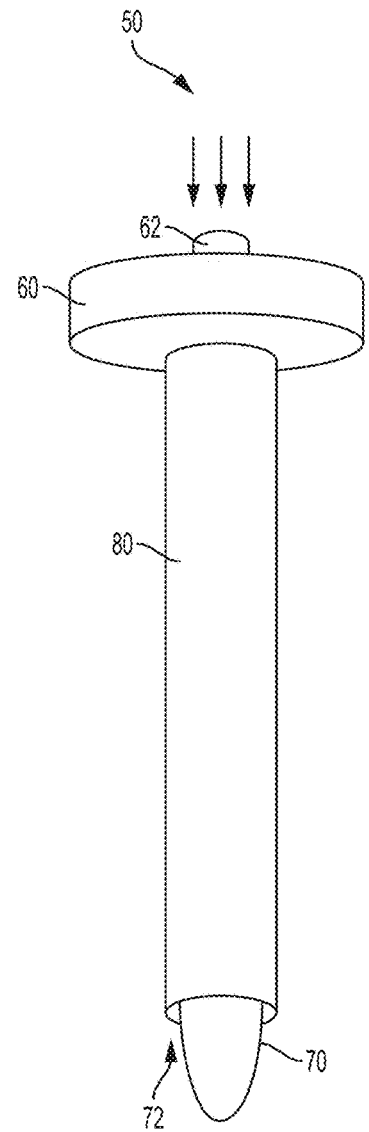

In some embodiments, the transfer apparatus may be configured for the transfer end to move between a retracted position and an extended position. FIGS. 9A-9B depict an example of such a transfer apparatus 50, where the handle end 60 includes an actuator 62 that is configured to cause suitable movement of the transfer end 70 between retracted and extended positions. As shown, the shaft 80 provides a housing for the transfer end 70, which is configured to move in and out of the housing.

FIG. 9A depicts the transfer apparatus 50 in a retracted position, where the housing shrouds the transfer end 70 therein. In some cases, it may be preferable for the transfer end to be kept covered until the desired time in which the sample material is to be collected, for example, to allow for sterile transfer from the substrate to the transfer apparatus.

Upon activation of the actuator 62 (e.g., pushing of a button coupled to the transfer end), as shown in FIG. 9B, the transfer end 70 moves away from the body of the transfer apparatus (e.g., away from the handle end 60 and shaft 80), to reach an extended position, protruding out from the distal tip 72 of the housing. Accordingly, the transfer end 70, when in the extended position, is exposed a sufficient amount for suitable collection of the sample material from a substrate.

The actuator for moving the transfer end may be constructed in any suitable manner. As noted, the actuator, when activated, may cause movement of the transfer end between the retracted position and the extended position. In various embodiments, the actuator may have any suitable component(s), such as one or more buttons, dials, switches, levers, or the like, that may be activated from the handle end, or other part of the transfer apparatus, for extending and/or retracting the transfer end. In some embodiments, the actuator may be configured to slide the transfer end back and forth between extended and retracted positions. Or, the actuator may include a ratcheting-type arrangement that suitably moves the transfer end through discrete positions toward extended or retracted positions, as desired. In some embodiments, the transfer apparatus may include multiple actuators. For example, an extending actuator may be configured to extend the transfer end outward (e.g., away from the handle end, or other part of the transfer apparatus), and a retracting actuator may be configured to retract the transfer end inward (e.g., toward the handle end, or other part of the transfer apparatus).

As an example, the actuator of the transfer apparatus may function similarly to a mechanical pencil or pen. As such, while not shown in the figures, the actuator may incorporate a ratcheting arrangement, as noted above, where the transfer end is held in place by a number of small jaws located near the tip of the housing. The jaws are controlled by a button on the end or the side of the housing or handle end. When the button is pushed, the jaws separate, pushing the transfer end forward (e.g., away from the handle end) toward an extended position, and further allows the transfer end to slide back and forth relative to the housing, as desired. When the button is released and the jaws retract, a retainer (e.g., rubber clamping device) located near the distal end of the housing grips the transfer end, keeping it in place. In another embodiment, a transfer end holder may be provided with ears or side projections that track along a helical channel provided within the handle end. In such an embodiment, a user may rotate a portion of the handle end while the transfer end holder is kept stationary, so as to suitably advance or retract the transfer end.

Figure 10A:
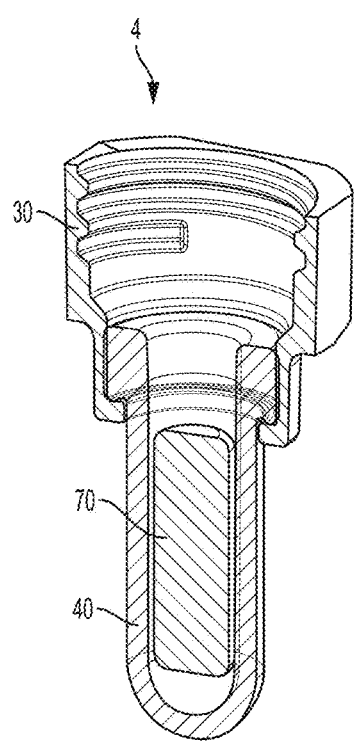
FIGS. 10A-10B illustrate use of another transfer apparatus in accordance with an embodiment.
Figure 10B:
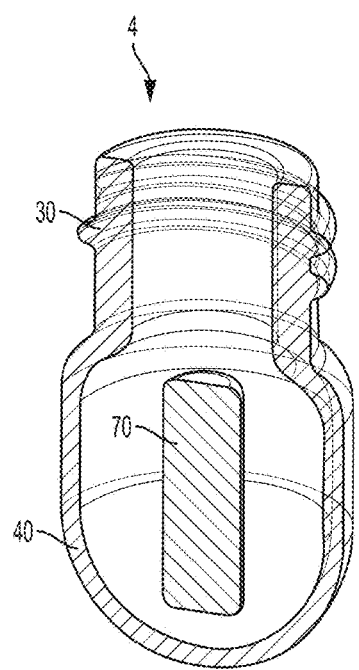

As noted above, for some embodiments, the transfer apparatus may be coupled to the vessel. For example, FIGS. 10A-10B illustrate various embodiments where the vessel 4 includes an entrance region 30, through which the transfer end and sample material may enter, and a body 40, where the transfer end and sample material are positioned during processing. In some embodiments, the handle end of the transfer apparatus may have a fastening region and the entrance portion of the vessel may have a corresponding fastening region. The corresponding fastening regions may be complementary to one another, providing for suitable attachment between the transfer apparatus and the vessel.

As shown in each of FIGS. 10A-10B, the entrance region 30 is threaded, to receive a cap having complementary threads, for engagement therewith. While not shown expressly in the figures, such a cap may be a part of the transfer apparatus. For example, the cap having a complementary threaded portion may be a part of the handle end of the transfer apparatus. Accordingly, the transfer apparatus and the vessel may be coupled together via mutual engagement of the complementary regions, and the transfer end may extend into the internal volume of the vessel. Or, the handle end of the transfer apparatus may be coupled to the vessel (e.g., at the entrance region) and, similar to certain embodiments described above, the transfer end may be separated from the handle end while the transfer end is located within the internal volume of the vessel.

Referring back to the illustrative embodiment shown in FIG. 1, the acoustic treatment system 100 includes an acoustic transducer 14 (e.g., including one or more piezoelectric elements) that is capable of generating an acoustic field (e.g., converging at a focal zone 17) suitable to cause mixing, vibration and/or other effects in a sample 1 held by a sample holder 4. While the sample holder 4 is shown in this embodiment to be a vessel (e.g., test tube, vial) that contains the sample 1, it can be appreciated that other sample holders and/or substrates may be used to hold or otherwise support the sample 1, as described further below.

The acoustic transducer 14 may produce acoustic energy within a frequency range of between about 100 kilohertz and about 100 megahertz such that the focal zone 17 has a width of about 2 centimeters or less. When formed, the focal zone 17 of the acoustic energy may be any suitable shape, such as spherical, ellipsoidal, rod-shaped, line-shaped, cigar-shaped, or column-shaped, for example, and may be positioned at least partially where the sample 1 is located. For instance, the transducer may have a curvature (e.g., dome, hemispherical, cylindrical, semi-cylindrical), or may otherwise be shaped or positioned in conjunction with a focusing element (e.g., lens, acoustic filter) that causes the formation of a particular pattern or shape of acoustic energy. In some embodiments, the transducer may be formed of a piezoelectric material, such as a piezoelectric ceramic. The focal zone 17 may be larger than the sample, or may be smaller than the sample, as shown in FIG. 1, e.g., the focal zone 17 may fit entirely within the sample holder 4. U.S. Pat. Nos. 6,948,843 and 6,719,449 are incorporated by reference herein for details regarding the construction and operation of an acoustic transducer and its control.

The sample holder 4 may have any suitable shape, size, material, or other arrangement/feature. While the sample holder is depicted as an enclosable container (e.g., glass tube, plastic container, well in a microtiter plate, plastic vial, vessel, 6×16 mm glass or plastic tube (e.g., less than 5 mL, less than 2 mL, less than 1 mL, less than 500 microliters, approximately 150 microliters in volume) having a screw cap, etc.) that may be supported at a location by a holder support 12, it can be appreciated that certain types of sample holders other than that shown may be used. For example, the sample holder 4 may be a cylindrical tube with a flat bottom and a threaded top end to receive a cap 9, may include a cylindrical collar with a depending flexible bag-like portion to hold a sample, may be a single well in a multiwell plate, may be a microscope slide, may be a cube-shaped sample holder, and/or may be of any other suitable arrangement. Or, as discussed above, the sample holder 4 may have a coupling portion (e.g., threaded, slotted, having a protrusion/ridge, fastening structure, etc.) at the entrance that is complementary to a coupling portion of the handle end of a transfer apparatus.

The sample holder may be structured to receive, at least, the transfer end of a transfer apparatus, for processing of a sample material located on the transfer end. In some embodiments, the sample holder may be a vessel defining an internal volume within which the transfer end carrying the sample material may be placed. In some cases, the sample holder may include a sealing member, such as a septum formed of an elastomeric material (e.g., rubber, silicone, etc.), that engages with an entrance, or other portion, of the vessel for sealing the internal volume from the external ambient environment. In an example, as described above, the sealing member may allow entry of the transfer end of the transfer apparatus, carrying sample material, into the internal volume of the vessel, and subsequent withdrawal (e.g., decoupling of complementary coupling portions) of the handle end from the transfer end. As a result, the transfer end and the sample material may remain within the vessel, and optionally sealed therein.

Sample holders and/or substrates described herein may be formed of glass, plastic, metal, composites, and/or any suitable combinations of materials, and may be formed by any suitable process, such as molding, machining, stamping, and/or a combination of processes. Sample holders, and the contents therein, may be tracked with suitable identification information, for example, labeled or printed thereon, for shipment and/or storage purposes.

The illustrative embodiment of FIG. 1 further shows the sample 1 to include a solid material 2, such as a tissue sample that has been formalin fixed and paraffin embedded (i.e., an FFPE sample) that is contained in a sample holder 4 along with a liquid 3, e.g., a non-solvent aqueous solution. The liquid 3 may be a mixture of water and detergent (e.g., 0.25% sodium dodecyl sulfate solution), although other solutions (e.g., solvent, non-solvent, buffer, etc.) are possible, or no solution at all. The liquid 3 may have any suitable volume, for example, less than 2 mL, less than 1 mL, less than 500 microliters, less than 100 microliters, approximately 50-80 microliters, etc.)

The sample may have any suitable volume and/or mass, e.g., the sample may be a so-called "scroll" or piece of FFPE tissue microtome sliced from a larger sample piece, a tissue sample taken by needle biopsy, or a sample produced by any other suitable method. In some embodiments, a sample cut by microtome may have a thickness of about 1 to 25 microns (e.g., 2-20 microns, 4 microns, 10 microns, etc.) and a length of 30 mm or less. For example, a sample may be sized to have a volume of about 4 cubic millimeters or less. Depending on the application or sample involved, other volumes may be used, such as a volume of less than 10 cubic millimeters, less than 30 cubic millimeters, less than 50 cubic millimeters, less than 100 cubic millimeters, or less than 500 cubic millimeters.

In some cases, care may be taken to suitably define a headspace 6 (shown to be a gaseous region immediately above the air-liquid interface 5) in the sample holder 4 prior to acoustic treatment. Accordingly, the cap 9 may include a lower portion, or extension 13, that reaches down into the space defined by the vessel.

In this illustrative embodiment, as discussed, the sample holder 4 may be associated with a holder support 12 (e.g., molded integrally, attached, welded, removably attached, etc.) that helps support the holder 4 during acoustic treatment. The holder support 12 may take any suitable arrangement or location, such as a ring-shaped element that is fixed relative to the vessel, as shown in FIG. 1. While embodiments described herein do not necessarily require a holder support 12, such a holder support 12 may serve to interface with the acoustic processing device so that the sample holder 4 and the sample itself may be positioned at a known location for processing/analysis, and relative to an acoustic field.

The acoustic treatment system 100 may also include a coupling medium container 15 that is capable of holding a medium 16, such as water or another liquid, gas (e.g., air, inert gas), gel (e.g., silicone), solid (e.g., elastomeric material), semi-solid, and/or a combination of such components, which transmits acoustic energy from the transducer 14 to the sample material 1 held within the sample holder 4.

In embodiments where the medium 16 includes a solid or semi-solid, or is otherwise able to retain its shape, a container 15 need not be provided, or a portion of the medium 16 itself may function as a container 15, e.g., to hold a liquid or gas portion of the medium 16. For example, in one embodiment, the transducer 14 may be attached to a solid coupling medium 16 (such as a silica or silicone material), which is also attached to a holder support 12, which may be formed, at least in part, by an opening or other feature of the medium 16. Thus, the transducer 14, medium 16 and holder support 12 may be formed as a single integrated part, if desired.

Due to the isothermal nature of the focused acoustic treatment, during acoustic processing, the temperature of the coupling medium may be maintained, without substantial fluctuation, as opposed to temperature changes that may otherwise occur from other methods of sample transfer. In some embodiments, the temperature of the coupling medium is maintained at a relatively low temperature, e.g., 40-60° C., although thermal control at lower or higher temperatures are also possible.

In some embodiments, for paraffin embedded samples, focused acoustic energy may be used to remove (or disassociate) paraffin from the tissue sample. Such removal may occur with or without hydration of the sample. Certain types of surfaces and substrates may promote, or exclude, transfer of the portion of the sample. Such transfer of a paraffin embedded sample may occur in a substantially dry environment, or a substantially wet environment. A substantially wet environment may provide for the ability for the sample to be rehydrated, with or without the presence of staining (e.g., immunohistochemical staining).

In some embodiments, appropriate parameters of the acoustic treatment system may be controlled, such as certain characteristics of the acoustic field and/or the relative position of the acoustic transducer 14 and the sample holder 4 (e.g., by moving the transducer, sample holder and/or the holder support). Accordingly, during acoustic processing, the sample may be positioned at a desired location relative to an appropriate focal zone 17. The transducer 14 may produce the focused acoustic energy to have a particular size and shape so that the focal zone is suitably positioned relative to the sample or initial substrate.

To control the acoustic transducer 14, the acoustic treatment system 100 may include a system control circuit 10 that controls various functions of the system 100 including operation of the acoustic transducer 14 and positioning of various components of the system (e.g., transducer, sample holder, etc.). The system control circuit 10 may provide control signals to a load current control circuit, which controls a load current in a winding of a transformer. Based on the load current, the transformer may output a drive signal to a matching network, which is coupled to the acoustic transducer 14 and provides suitable signal(s) for the transducer 14 to produce desired acoustic energy.

The system control circuit 10 may control various functions of the acoustic treatment system 100. For instance, the figures show a dashed line linking the control circuit 10 to the holder support 12, schematically representing an optional positioning system, e.g., which may include a robot, gantry, screw drive, or other arrangement to move the holder support 12. The system control circuit 10 may be configured to receive operator input, such as commands for system operation, or automatically provide input. The system control circuit 10 may output appropriate information in a suitable manner (e.g., to a visible display screen, as indicator lights, etc.). Such information may include sample treatment status information in electronic data form, suggestions/recommendations for applying further acoustic treatment, or other information that may be made available.

In an example, slices of kidney tissue 5 microns thick, provided by BIOCHAIN®, were mounted on to glass slides. The glass slides were placed on a heating block set at a temperature of 40° C. A transfer apparatus having a transfer end that includes a microfibrous web of POREX® fibers soaked in 3 microliters of sodium dodecyl sulfate buffer was used to collect the tissue samples from the glass slides. In this example, the microfibrous web was approximately 10 mm in length, however, during collection of sample from the substrate, approximately 3 mm in length of the was exposed from the transfer end holder. In addition, the fibers of the transfer end were stiff enough to dislodge the tissue samples from the glass slides.

The entire 10 mm length microfibrous transfer end was dropped, with the collected tissue sample, into a COVARIS® microTUBE, configured to be compatible with focused acoustic processing. 100 microliters of sodium dodecyl sulfate buffer was located within the microTUBE, for subsequent focused acoustic treatment. DNA was then extracted from the tissue sample using a COVARIS® truX-TRAC™ FFPE DNA Kit with a COVARIS® S220 Focused-ultrasonicator.

The yield of DNA from the kidney tissue samples using the microfibrous transfer end was comparable to the total yield when a metal razor blade was used. However, use of the microfibrous transfer end resulted in an overall reduction in the likelihood of sample contamination and minimal charge build up on the sample. While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

What is claimed is:

1. An acoustic treatment system, comprising:
    a transfer apparatus including:
        a transfer end constructed and arranged to be placed in contact with a sample material supported by a substrate, for transfer of at least a portion of the sample material from the substrate to the transfer end,
        a handle end located opposite the transfer end, the handle end arranged to be manipulated by hand,
        a first coupling portion connected to the transfer end, and
        a second coupling portion connected to the handle end and complementary to the first coupling portion, the first and second coupling portions constructed and arranged to be coupled to and decoupled from each other;
    a vessel defining an internal volume for holding the transfer end of the transfer apparatus; and
    an acoustic energy source configured to generate focused acoustic energy having a frequency of about 100 kHz to 100 MHz through a wall of the vessel to expose the portion of the sample material to a focal zone of acoustic energy while the transfer end of the transfer apparatus and the portion of the sample material are located within the internal volume of the vessel.

2. The system of claim 1, wherein the transfer end of the transfer apparatus includes a microfiber composition configured to adhere to and collect the portion of sample material from the supporting substrate.

3. The system of claim 1, wherein the transfer end of the transfer apparatus includes at least one of a non-woven hydrophobic material, polyester, polyethylene, polypropylene, polytetrafluoroethylene and nylon.

4. The system of claim 1, wherein the transfer end of the transfer apparatus includes at least one of a swab, fabric and fibrous web configured to adhere to and collect the portion of sample material from the supporting substrate.

5. The system of claim 1, wherein the internal volume of the vessel is less than 5 mL and the transfer end of the transfer apparatus is constructed and arranged to fit within the internal volume of the vessel.

6. The system of claim 1, further comprising a solution in contact with the sample material supported by the substrate, the solution including at least one of limonene, a surfactant, citric acid and a buffered solution.

7. The system of claim 1, wherein the sample material includes a formalin fixed, paraffin embedded tissue.

8. The system of claim 1, wherein the vessel includes a sealing member constructed and arranged to accommodate entry of the transfer end of the transfer apparatus into the internal volume of the vessel and to seal the internal volume of the vessel, including the transfer end and the portion of the sample material, from an external environment.

9. The system of claim 1, wherein coupling of the first and second coupling portions together forms a rigid connection between the transfer end and the handle end.

10. The system of claim 1, wherein the handle end of the transfer apparatus is constructed and arranged to be coupled to an entrance portion of the vessel.

11. The system of claim 10, wherein the handle end of the transfer apparatus has a first fastening region and the entrance portion of the vessel has a second fastening region complementary to the first fastening region, wherein the first and second fastening regions are constructed and arranged to be fastened to each other.

12. The system of claim 1, wherein the transfer apparatus includes an actuator coupled to the transfer end, the actuator configured to manipulate a position of the transfer end between a retracted position and an extended position.

13. A transfer apparatus, comprising:
    a transfer end constructed and arranged to be placed in contact with a sample material supported by a substrate, for transfer of at least a portion of the sample material from the substrate to the transfer end;
    a handle end located opposite the transfer end, the handle end arranged to be manipulated by hand;
    a first coupling portion connected to the transfer end;
    a second coupling portion connected to the handle end and complementary to the first coupling portion, the first and second coupling portions constructed and arranged to be coupled to and decoupled from each other; and
    an actuator coupled to the transfer end, the actuator configured to manipulate a position of the transfer end between a retracted position and an extended position.

14. The apparatus of claim 13, wherein the actuator is configured to cause movement of the transfer end away from a body of the transfer apparatus.

15. The apparatus of claim 13, wherein the actuator includes a button that, when pressed, is configured to cause movement of the transfer end between the retracted position and the extended position.

16. The apparatus of claim 13, wherein the actuator includes a ratchet arrangement configured to cause movement of the transfer end a discrete distance away from a body of the transfer apparatus.

17. The apparatus of claim 13, further comprising a housing constructed and arranged to cover at least a portion of the transfer end when in the retracted position, and permit exposure of the transfer end to the sample material when in the extended position.

18. The apparatus of claim 13, wherein the handle end is constructed and arranged to be coupled to an entrance portion of a vessel defining an internal volume for holding the transfer end of the transfer apparatus.

19. The apparatus of claim 13, wherein the transfer end of the transfer apparatus includes a microfiber composition configured to collect the portion of sample material from the supporting substrate.

20. The apparatus of claim 13, wherein the transfer end of the transfer apparatus includes at least one of a non-woven hydrophobic material, polyester, polyethylene, polypropylene, polytetrafluoroethylene and nylon.

21. The apparatus of claim 13, wherein coupling of the first and second coupling portions together forms a rigid connection between the transfer end and the handle end.

* * * * *